United States Patent [19]

Fabricius et al.

[11] Patent Number: 4,808,533

[45] Date of Patent: Feb. 28, 1989

[54] METHOD OF PREVENTING T-CELL BLASTOGENESIS

[75] Inventors: Hans-Ake Fabricius, Breisach; Eckart U. Köttgen, Freiburg, both of Fed. Rep. of Germany

[73] Assignee: Shanksville Corporation NV, Netherlands, Netherlands Antilles

[21] Appl. No.: 730,042

[22] Filed: May 3, 1985

Related U.S. Application Data

[62] Division of Ser. No. 514,197, Jul. 15, 1983, Pat. No. 4,661,447, which is a division of Ser. No. 255,251, Apr. 17, 1981, Pat. No. 4,406,830.

[51] Int. Cl.$^4$ .................. C12N 5/00; C12N 9/99
[52] U.S. Cl. .................. 435/240.2; 435/184; 435/240.1; 514/885
[58] Field of Search .................. 435/240, 241, 29, 32, 435/240.1, 240.2, 184; 514/139, 706, 710, 739, 885; 436/503

[56] References Cited

U.S. PATENT DOCUMENTS

| | | | |
|---|---|---|---|
| 4,406,830 | 9/1983 | Fabricius | 530/380 |
| 4,661,447 | 4/1987 | Fabricius | 435/68 |
| 4,681,844 | 7/1987 | Fabricius | 435/68 |

OTHER PUBLICATIONS

Chang et al., "Effects of Nα-Tosyl-L-Lysyl--Chloromethyl-Keton on the Activity of Cytotoxic T Lymphocytes", *Journal of Immunology*, vol. 124(3), Mar. 1980, pp. 1028–1033.

Levy et al., "Effect of N-Acetylcystein on Some Aspects of Cyclophosphamide–Induced Toxicity and Immunosuppression", *Biochemical Pharmacology*, vol. 26, 1977, pp. 1015–1020.

Schwartz, A. et al., Journal of Immunology, 117(3); 871–875, (9–1976).

*Primary Examiner*—Margaret Moskowitz
*Attorney, Agent, or Firm*—Sherman and Shalloway

[57] ABSTRACT

A cell mediated immune response system glycoprotein having a molecular weight of about 90,000 and having at least one sialic acid moiety as a biologically active site is disclosed. The glycoprotein is specifically bound by wheat germ agglutinin and also by the hydrophobically binding ligand Blue A (Cibacron Blue F3G-A) but does not bind to lysine. The glycoprotein is a necessary cofactor with Interleukin-1 in the biosynthesis of T-cell growth factor (I1-2). A process for producing a serum-free and mitogen-free I1-2 in vitro by adding the glycoprotein to a serum-free and mitogen-free interleukin-1 preparation is described. The method for producing the serum-free and mitogen-free Interleukin-1 is also described. A chemically defined T-cell growth culture medium containing the new glycoprotein as the only protein substance is used in the above process and also provides a means for studying regulation of T-cell lymphocyte growth. Inhibitors for the formation of T-cell blasts in cell mediated immunological response provide a powerful new tool for preventing host-graft rejection. These inhibitors are alkylating agents for serine esterase enzymes which have been found to be involved in the cell mediated immunological response system which generates natural Killer (NK) cells, the latter being responsible for graft rejection in a host.

2 Claims, 4 Drawing Sheets

METHOD OF PREVENTING T-CELL BLASTOGENESIS

This is a division of application Ser. No. 514,197, filed July 15, 1983, now U.S. Pat. No. 4,661,447, which is a division of application Ser. No. 255,251, filed Apr. 17, 1981, now U.S. Pat. No. 4,406,830.

BACKGROUND OF THE INVENTION

This invention relates to a newly discovered blood serum protein which is part of the T-cell regulating system; to the use of this novel protein in the production of a serum-free and mitogen-free preparation containing Interleukin-I and serum-free and mitogen-free preparation containing T-cell growth factor; to a chemically defined T-cell growth culture medium containing the novel protein as the only protein; and to the novel protein in a purified form.

A serum-free, mitogen-free T-cell growth factor (Interleukin-2 or Il-2) has been described in the pending application of Hans-Ake Fabricius and Roland Stahn, titled A SERUM-FREE AND MITOGEN-FREE T-CELL GROWTH FACTOR AND PROCESS FOR MAKING SAME, filed Mar. 24, 1981 now U.S. Pat. No. 4,390,623 (filed as a continuation-in-part of application Ser. No. 193,112, filed Oct. 2, 1980, abandoned). The disclosures of these prior applications are incorporated herein, in their entirey by reference thereto.

The preparation of the T-cell growth factor described in these prior applications includes a step of stimulating isolated lymphocytes (e.g. peripheral mononuclear blood cells) in the presence of serum and mitogen such as phytohemagglutinin A (PHA). In fact, all known published literature on the production of lymphokines from lymphocytes reports the step of contacting the lymphocytes with mitogen in the presence of blood serum, added as a supplement to the culture medium.

While such procedures produce Il-2 in significant yields the presence of serum has the drawbacks referred to in the above-mentioned prior applications, namely the presence of numerous proteins which may mask the true effect of Il-2; allergic and anaphylactic reactions in patients repeatedly given injections of serum-containing preparations; and the inability to concentrate serum-containing preparations since the serum will precipitate and plug the pores of the filters used for this purpose. Despite these drawbacks it had always been presumed that the presence of serum was essential for the production and maintenance of growing T-cell lines by the T-cell growth factor (Il-2). However, the inventors of the above mentioned prior applications have been able to show that serum-free and mitogen-free Il-2 preparations can be used to maintain growing T-cell lines, and thereby provide a means for combatting tumor growth.

Nevertheless, the procedure described in the prior applications which required the lymphocyte stimulating step in the presence of serum was somewhat cumbersome in requiring the essentially complete removal of the serum prior to incubating the stimulated cells in a serum-free, mitogen-free liquid culture medium.

The present inventors conceived the idea that it might be possible to completely eliminate the use of serum in the stimulation of the lymphocytes. In order to test this idea it was first attempted to test the effect of specific fractions of human serum which had been separated in narrow molecular weight ranges by gel partition chromatography. Quite surprisingly it was found that only the molecular weight fraction of the serum in the range of from about 60000 to 130000 was capable of inducing production of Il-1. However, none of the known blood serum proteins in this molecular weight range, e.g. transferrin, haptoglobin, albumin, etc. were found to be capable of inducing the production of Il-2 in bioassay tests in culture medium. This observation led the inventors to the conclusion that an unidentified blood serum factor must be present in the serum and must be necessary for the stimulation of lymphocytes to produce T-cell growth factor (also known as TCGF or Il-2). In fact, such previously unidentified and unknown blood serum factor has now been isolated and provides the basis of the present invention.

SUMMARY OF THE INVENTION

According to the present invention, a previously unknown unidentified blood serum protein (glycoprotein) having a molecular weight of about 90,000 Daltons and having at least one sialic acid (N-acetyl neuraminic acid) residue is provided. This protein is further characterized by its relative heat stability—it loses less than one-half of its biological activity when heated at 80° C. for 30 minutes; and by its strong affinity to lectins, primarily wheat germ agglutinin (WGA), and to hydrophobically binding ligands such as Blue A, which are commercially readily available; but no specific binding to lysine.

In another aspect this invention provides a process for producing serum-free, mitogen-free Interleukin-1 (Il-1) (also known as lymphocyte activating factor LAF) and serum-free, mitogen-free Il-2 by incubating peripheral mononuclear blood (PBL) cells in a serum-free liquid tissue culture medium to remove residual serum proteins on the surfaces of the PBL cells, activating the incubated cells with a mitogen, washing the activated cells with a sterile liquid to remove the mitogen from the cells and conditioning the serum-free mitogen-free activated cells in a liquid tissue culture medium to produce a serum-free, mitogen-free Interleukin-1 (Il-1); contacting the Il-1 containing liquid tissue culture medium with the novel blood serum glycoprotein of this invention; and incubating the cells in the presence of Il-1 and the novel blood serum glycoprotein to induce synthesis of Il-1 and to transfer the Il-2 (T-cell growth factor) from the cells to the liquid phase of the tissue culture medium to thereby produce a serum-free, mitogen-free Il-2.

In still another aspect this inventio provides a chemically-defined liquid tissue culture growth medium for growing lymphocytes in vitro. The medium includes the conventional cell nutrients and as the only protein constituent of the medium the novel blood serum protein of this invention. This tissue culture growth medium can then be used to grow T-cells in the absence of blood serum.

Such a medium is beneficial for studying regulation of T-lymphocyte growth in a chemically defined surrounding, and offers the advantage of being less dangerous with respect to hepatitis than media containing human whole serum.

A still further aspect of this invention relates to process for inhibiting the in vivo production of natural killer cells by interfering with the cell mediated immunological system response mechanism to invasion by foreign bodies, particulary grafts of tissue or other organs. According to this process a serine alkylating agent is used to prevent blastogenic transformation of T-cells to T-blasts.

BRIEF DESCRIPTION OF THE DRAWINGS

The invention will now be explained in greater detail by the following description and specific embodiments and with the aid of the accompanying drawings in which.

DETAILED DESCRIPTION OF THE INVENTION AND PREFERRED EMBODIMENTS

Figure 1:
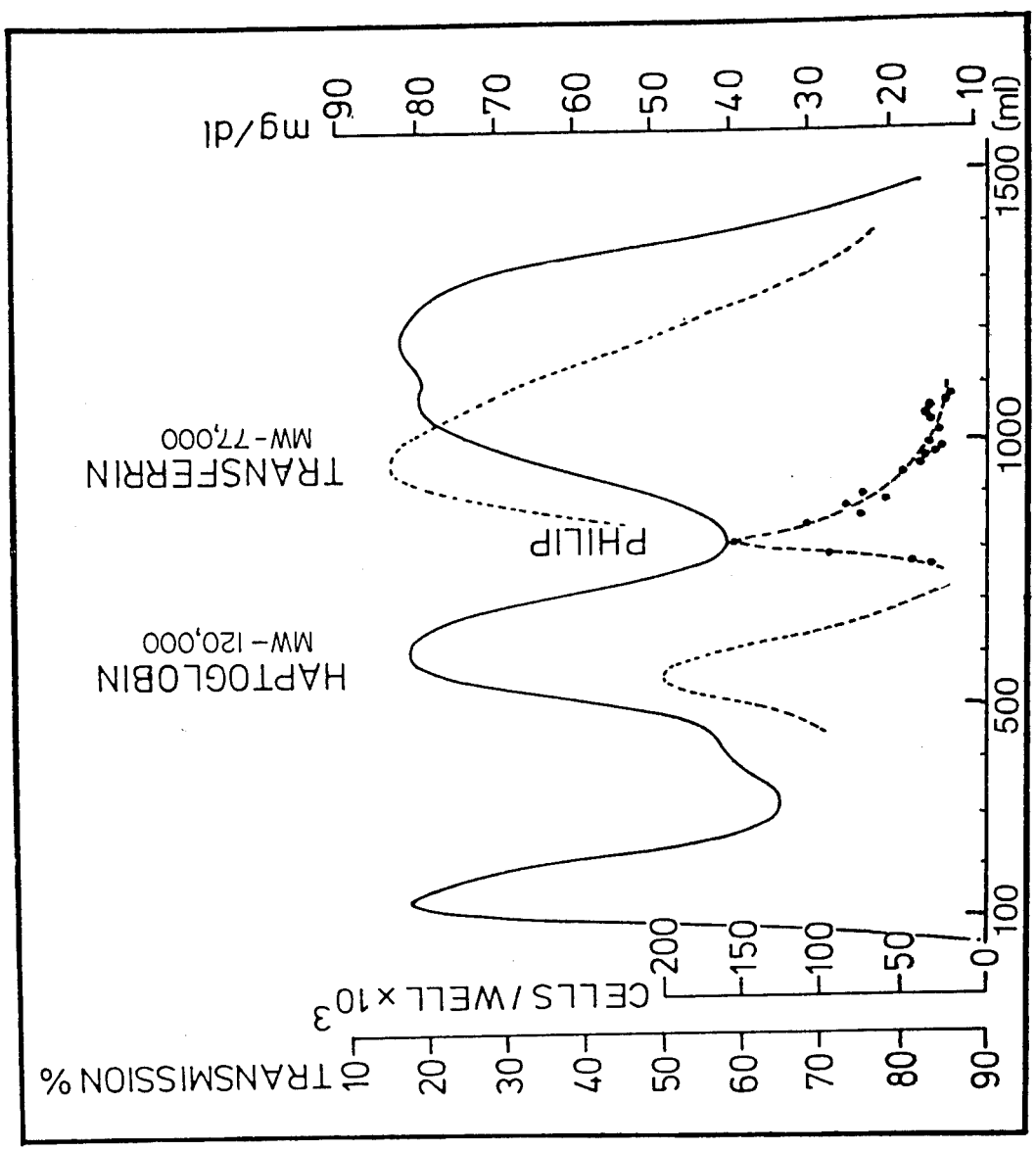
FIG. 1 is a plot of light transmission(%) versus elution volume for separation of human blood serum on a Sephadex G 200 chromatography column and also showing the biologically active peak for the novel blood serum glycoprotein of this invention and also the peaks for transferrin and haptoglobin.

It has been demonstrated in the literature and also shown in the data reported in the above-mentioned applications of Fabricius and Stahn that tumor patients are defective in the ability of their cellular immune system (cell mediated immunity) to produce the T-cell growth factor (Il-2) necessary for production of natural killer cells which can attack and destroy tumors. Therefore, if the natural killer cells in tumor patients can be stimulated into activity, it should be possible to stop the growth of tumor cells.

According to current theory of the cell mediated immunological response mechanism to invasion of the host by a mitogen, the mitogen activates a macrophage subpopulation of lymphocytes to produce Il-1 (Interleukin I) which in turn stimulates a T-cell subpopulation, presumably T-helper cells, to produce Il-2. The latter is identified biologically by its ability to support the growth of permanently growing T-cell lines.

Contrary to this current belief it has now been found that production of Il-2 not only depends on the interaction of T-lymphocytes with Il-1 but also with a previously unknown unidentified protein found in blood plasma sera from humans as well as from other mammals, such as horse sera and bovine sera. This protein has a molecular weight of about 90,000. Thus, when Il-1 is brought into contact with lympocytes in the absence of serum or with serum from which the molecular weight fraction range of 86,000 to 94,000 has been eliminated by fractionation Il-2 production is not observed. As far as applicant is aware this observed phenomenon has never been reported or suggested in the literature.

In order to determine whether this "comitogenic" blood serum factor was one of the known blood serum proteins in the molecular weight range where the biological activity was found a series of bioassay tests were carried out by adding the known proteins—albumin, transferrin, plasminogen and haptoglobin—to and Il-1 conditioned serum-free cell culture medium. None of these known proteins were capable of forming T-cell blasts or sustaining T-cell lines. Accordingly, it was concluded that none of these proteins were capable of interacting with Il-1 on the T-cell lymphocytes to produce Il-2 (Il-2 by definition is capable of sustaining the growth of T-cell lines).

The unknown "comitogenic" factor was determined to be a protein by virtue of the fact that the biological activity of the "comitogenic" factor-containing blood serum fraction was destroyed by treatment with trypsin. Since trypsin only deactivates proteins (by destroying the peptide bonds) the unknown factor must be a protein.

Further investigation revealed the presence of at least one sialic acid residue (N-acetyl neuraminic acid). Thus, treatment of the novel comitogenic protein factor with neuraminadase enzyme resulted in a lose of biological activity.

By the reaction of the comitogenic protein factor with various lectins it has been further identified as a glycoprotein although the specific sugar moiety has not yet been identified.

Since the comitogenic glycoprotein was originally found in human blood sera it has been given the acronym PHILIP: Plasmatic Human Interleukin Inducing Protein. Accordingly, the name PHILIP may be used to identify the previously unknown and unrecognized blood serum protein which can be characterised by its physico-chemical properties: molecular weight of about 90,000 D; glycoprotein; at least one sialic acid residue; strong adherence (binding) to lectins such as wheat germ agglutinin, and Blue A; and relative heat stability; and by its biological activity: in the presence of Interleukin-I (serum-free and mitogen-free) will induce peripheral monuclear blood cells (lymphocytes: T-cells) to produce T-cell growth factor (Il-2) which forms T-cell blasts and supports the growth of T-cell lines; alternatively, in a serum-free system, in the presence of mitogen, such as PHA and peripheral mononuclear blood cells, PHILIP will induce the production of Il-2 and T-cell blastogenesis. In the latter case the PHA first induces the pro-macrophage cells to produce Il-1, which, with the coaction of PHILIP, induces a second cell fraction, presumably T-helperr cells to produce Il-2.

At this point it should be emphasized that the mechanism by which PHILIP functions to cooperate with Il-1 and the T-cells to produce Il-2 has not been elucidated. It is generally believed, but has not yet been proven conclusively, that the subpopulation of T-cells known as T-helper cells produce Il-2.

The production of an Il-1 preparation which is serum-free and mitogen-free is an important and novel aspect of this invention. Since Il-1 preparation can be used directly, or after being concentrated (which is made possible by being serum-free) for production of Il-2.

The serum-free mitogen-free Il-1 can be prepared from isolated adherent (pro-macrophage) cells or directly from peripheral mononuclear blood cells (PBL). To isolate the adherent (pro-macrophage) cells the following well known technique can be used: Peripheral mononuclear blood cells are first isolated from the blood by the density gradient technique. For example, the blood is layered into a tube containing a high density polymeric solution, such as the commercially available Ficoll-hypaque, and centrifuged. The PBL cells are collected above the polymeric solution and are carefully removed. The Ficoll-hypaque solution is slightly toxic so the removal must be done very carefully. The so-obtained PBL are washed several times, usually three times, with a sterile solution to ensure complete removal of the Ficoll-hypaque solution. The washing is accomplished by gently suspending the cells in the sterile solution and centrifuging to again separate the cells from the solution. Low centrifuge speed and time (e.g. $300\times G$ for ten minutes) are used to avoid breakage or destruction of the cells. Rosewell Park Memorial Institute (RPMI) 1640 is a commercially available sterile solution which can be used for this purpose and also as the liquid culture medium. Machines are presently available for the automatic separation of mononuclear cells from blood and such machines are advantageously used when available.

The PBL cells are then placed in plastic Petri dishes and incubated for about 1 hour at about 37° C. The pro-macrophage cells are adherent to plastic and adhere to the walls of the Petri Dishes. The non-adherent cells are washed off by spraying with sterile solution, e.g. RPMI 1640.. The adherent cells are removed from the Petri dish. A rubber policeman can conveniently be used for this purpose.

The recovered pro-macrophage cells, after being counted (usually about $3\times 10^6$ cells per ml are used) are incubated for from about 18 to 24 hours at about 37° C. using a non-supplemented liquid culture medium, such as RPMI-1640. Fresh culture medium can be added to or replace used culture medium every few hours if desired. By "non-supplemented" is meant that no mitogenic substances or blood serum is added to the culture. All incubation steps in this invention are carried out under a $CO_2$ (about 5-15%) atmosphere and a temperature of about 37° C., unless otherwise noted.

The purpose of this preliminary incubation step is to remove any serum proteins which may have been present on the cell membrane surfaces. Since the cell membranes are regenerated about once every eight hours the membranes will "turn over" about 2 or 3 times during this incubation period.

When using the PBL cells without separation of the adherent pro-macrophage cells the PBL cells can be directly incubated under the same conditions as described above to remove any proteins which may be present on the surface (membrane) of the cells. The cells are now ready to be activated for production of Il-1.

Activation of the cells is accomplished by contacting the cleaned cells in the liquid culture medium with a mitogen. Phytohemagglutinin A (PHA) is preferably used for this purpose although other lectin type mitogens, such as concanavalin A (Con A), *Escherichia coli* lyipopolysaccharide (LPS) and pokeweed mitogen (PWM) can also be used. An important feature of the invention is that the mitogen is only left in contact with the cells for a short period of time, preferably about 4 hours although longer times up to about 12 hours can be used. Since the cells are activated or stimulated for and actually begin production of Il-1 during this short time period the mitogen is removed from the cells without significantly limiting the production of Il-1.

The washing can be accomplished as described above for removing the Ficoll-hypaque solution, i.e. centrifuging the cell suspension, adding the cells to fresh sterile solution, and repeating this process about 3 times. The supernatants can be saved for future cell stimulations or for recovery of Il-1 or PHA.

The activated cells can then be conditioned by incubating the cells in a fresh non-supplemented RPMI 1640 for about 12 to 30 hours, preferably about 15 to 26 hours, most preferably about 14–24 hours. Generally, the cells are used in a concentration of about $3\times 10^6$ cells per ml of culture medium.

A serum-free lectin free Il-1 is obtained in the supernatant. The presence of Il-1 is confirmed by known chemical and biological characteristics of Interleukin-1. Thus the product has been shown by the results of contacting with protease and lectins to be a non-glyco group (i.e. sugar-free) protein and by gel filtration chromatography to have a molecular weight of approximately 15,000. The biological characteristics of the Il-1 preparation are also consistent with the definition of Il-1:

in the presence of blood serum T-cell blastogenesis is induced;

it is not able to support the growth of a permanently growing T-cell line.

In the present invention biological activity is determined by a standardized bioassay test which is carried out as follows:

Peripheral mononuclear blood cells which have been isolated and subjected to preliminary incubation to remove serum protein and macrophage cells adhered to the surface of the lymphocyte cells, as described above, are suspended in RPMI 1640 to provide a cell density of one million cells per ml of culture medium.

The supernatant whose biological activity is being assayed is deposited in the first row of a microtiter plate. The second row of wells is filled with RPMI to provide a concentration which is one half that of the first row. Similarly, the third and each succeeding row is filled with supernatant diluted to a concentration which is one-half of the preceding row. As a result, a microtiter plate is obtained wherein a dilution factor of 1:2 is obtained as one moves from the top towards the bottom of the plate.

A measured number of the mononuclear cells which have been preliminarily incubated is added to each well in the microtiter plate. The growth of the cells as a result of stimulation by T-cell growth factor (Il-2) is monitored. In the case of bioassay for Il-1 it is further necessary to add serum or PHILIP to each well since otherwise Il-2 production will not occur. Generally serum is used from a human serum pool in an amount of 15% vol/vol. Likewise, in the bioassay for the biological activity of PHILIP either mitogen (PHA) or Interleukin-1 (serum-free) must be added to each well containing the isolated peripheral mononuclear blood cells.

Significant activity is considered to be present in those titer rows where cell density has doubled at the end of seven days. The inverse of dilution for those rows are used as the measure of significant growth.

The serum-free lectin-free Il-1 preparation so obtained, after concentration if desired, is used to produce Il-2 by contacting lymphocytes in the presence of PHILIP. In terms of biological activity PHILIP can be used directly after separation of the appropriate molecular weight fraction by, for example, gel chromatography, for example separation on a Sephadex G-150 or G-200 column (Sephadex is a bead-formed, dextran gel prepared by cross-linking selected dextran fractions with epichlorhydrin; Sephadex is a trademark of Pharmacia AB, Uppsala, Sweden). Alternatively the PHILIP containing serum fraction is dialyzed against RPMI for about 24 hours using a membrane passing substances having molecular weights below about 10,000 to 15,000 prior to use.

However, it is preferred to use PHILIP after removal of other blood serum proteins contained in the PHILIP-containing fraction. Since PHILIP is highly adherent to various lectins this property is utilized to purify PHILIP by affinity chromatography using the lectin as the immobilized ligand to which the glycoprotein PHILIP is specifically (but reversibly) binding. Sepharose (a bead formed agarose gel; a trademarked product of Pharmacia AB) beads have been used as the insoluble matrix to which the ligand is immobilized. Among the ligands to which PHILIP is selectively binding are Blue A, and wheat germ agglutinin (WGA). Blue A-Sepharose and WGA-Sepharose are available from Pharmacia Fine Chemicals AB. Wheat germ agglutinin is the preferred lectin since other blood serum proteins of similar molecular weights, e.g. plasminogen, transferrin, and albumin are either only weakly binding or nonbinding to WGA. In particular the following affinities of blood serum proteins to various Sepharose type affinity column gel beads can be noted:

| Protein | Ligand bound to Sepharose | | | |
|---|---|---|---|---|
| | ConA | WGA | Blue A | Lysine |
| PHILIP | + | ++ | ++ | − |
| Plasminogen | + | + | − | ++ |
| Transferrin | ++ | + | − | − |
| Albumin | − | − | ++ | − |

Notes:
++ 85% of the protein is specifically bound
+ partial specific binding
− non specific binding It can be seen from the above table that PHILIP can be easily separated from other blood serum proteins in the same molecular weight range by affinity chromatography using WGA Sepharose. The following procedure can be used.

The biologically active fraction (capable of inducing Il-2 production in the bioassay test) recovered from a Sephadex G200 column is incubated on a WGA Sepharose column at room temperature for about 1 hour. The column is then eluted with two buffers. In the first elution a normal phosphate buffer (pH=7.2) is used at a 10-fold volume (100 ml buffer)/10 ml WGA Sepharose). The first elution removes all proteins which are not specifically bound by WGA.

The second elution is performed with the same phosphate buffer to which is added N-acetyl-D-glucosamine (NADG) at about 20 mM NADG per liter of buffer. In the first step a 5-fold volume is used (50 ml buffer/10 ml WGA Sepharose) and this removes those proteins binding only weakly to WGA. In the second step a 5-fold volume is again used to remove all proteins with high specific binding affinity to WGA. Accordingly, essentially pure PHILIP can be obtained by the present invention.

The present invention also provides a process for producing serum-free and mitogen and lectin free Interleukin-2 (Il-2 or TCGF) using PHILIP and the serum-free lectin-free Il-1 preparation previously described. According to this process the serum-free lectin-free Il-1 preparation is mixed with a PHILIP-containing liquid culture medium (e.g. RPMI 1640) preparation at a volumetric mixing ratio of from about 1:1 to 1:32, preferably from about 1:1 to 1:4, most preferably about 1:1.

The serum-free lectin-free Il-1 preparation can be used directly after the conditioning step without the Il-1 containing supernatant from the cells. In this case these cells will be activated to produce Il-2. Alternatively, the supernatant can be collected by centrifugation or filtering and a fresh supply of isolated lymphocytes provided. It is also possible to supply additional isolated lymphocytes to the conditioned Il-1 culture medium without removing the cells already contained therein.

Although a purified PHILIP preparation can be used it is also possible to use biologically active serum fraction from the gel chromatography separation. For example, if the separation is performed on a Sephadex G-200 column the elution profile shows three peaks. Biological activity is found in the eluted fractions corresponding to the left shoulder of the third peak. Therefore, by collecting those fractions corresponding to the valley between the second and third peaks through the top of the third peak substantially all of the biologically active T-cell regulating blood serum protein PHILIP will be recovered. These eluted fractions can then be concentrated by a factor of about 10-fold (corresponding nearly to the original concentration) by filtering through an appropriate filter such as Amicon YM10. The concentrated serum is then dialyzed against the sterile liquid culture medium, e.g. RPMI 1640. The amount of liquid culture medium to which the PHILIP containing serum fraction is added need only be that amount which gives an equivalent biological activity (as determined by the microtiter bioassay test described above) as the Il-1 preparation. However, greater or lesser amounts can be used.

This mixture is used to incubate isolated blood lymphocytes at standard tissue culture conditions: 98% humidity, 7,5% $CO_2$, temperature 37° C., for about 8 to 24 hours, preferably about 8 to 18 hours.

After conditioning of the lymphocytes, specifically T-cells (presumably T-helper cells) by the incubation, the cells are separated from the culture medium as by centrifugation for example. Some serum-free (or substantially serum-free, depending on the source of PHILIP) and mitogen-free T-cell growth factor (Il-2) will be present in the supernatant since production of IL-2 can be expected to begin within a few minutes to about 1 hour after initiation of incubation.

The separated conditioned cells are repeatedly washed, for example 3 times, with fresh RPMI-1640 or other suitable liquid tissue culture medium. These cells can then be recycled for further conditioning.

The biological activity of the resulting serum-free and mitogen-free Il-2 containing supernatant can be determined by the bioassay test described above.

The liquid tissue culture medium to which pure PHILIP has been added provides a useful chemically defined T-cell growth culture medium which allows for a more precise study of the regulation of T-lymphocyte growth since the surroundings are not contaminated by other, usually undefined, proteins, as would be the case if whole serum was used. Furthermore, since human whole serum is not used the danger of transmitting hepatitis virus is substantially eliminated.

Thus, in addition to PHILIP the liquid tissue culture medium will contain liquid solvent, water, and conventional cell nutrients such as amino acids, vitamins, glucose, saline and a buffer system.

As described in the previously mentioned prior applications of Fabricius and Stahn the serum-free and mitogen-free T-cell growth factor finds utility in numerous areas including, for example, diagnosis and treatment of immune deficiency in tumor patients. Another application of Il-2 described in the prior applications is in the field of organ transplantation. In this regard it was described that Il-2 can be used as an antigen to develop antibodies in animals which could be used to inhibit graft rejection which is a well-known cell mediated response.

It has now been found, however, that it is possible to directly interfere with the ability of the immunological system to form natural killer cells by adding to the blood serum a serine alkylating agent. Although is is not entirely clear how the serine alkylating agent functions to prevent T-cell blastogenesis it is presently believed that the T-cell growth factor (Il-2) is a serine esterase enzyme which is inhibited from sending signals to the T-effector cells since the serine active site is blocked by the alkylating agent. In any case, whether the Il-2 is itself a serine esterase, which is deactivated or a serine esterase is present in the serum as a comitogenic factor and this factor is prevented from cooperating with Il-2 to cause T-cell blast formation, or whether the serine alkylating agent prevents biosynthesis of Il-2 or modifies the surface of the T-effector cell or accomplishes its inhibitory effect in some other manner, it has nevertheless been demonstrated in numerous experiments that the serine alkylating agent inhibits blast transformation of pre-incubated T-cells in the presence of Il-1 and PHILIP or Il-1 and whole blood serum from humans or other animals, e.g. bovine animals.

Serine alkylating agents which can be used as the T-blast inhibition include diisopropylfluorophosphate (DFP), phenylmethylsulfonic fluoride and the like.

It is interesting to note that plasminogen is a serine esterase. However, since it has already been found that Il-2 production and T-cell blastogenesis will take place in the absence of plasminogen it is clear that the serine alkylating agent's reaction with plasminogen is not responsible for the inhibition of blastogenesis.

EXAMPLE 1

Gel partition chromatography on human blood serum. Batches of 50 ml whole human serum are applied to a Sephadex G-200 column (50×1200 mm) (from Pharmacia AB, Uppsala, Sweden) equilibrated with 0,05 M phosphate buffer containing 0,1 NaCl; flow rate 60 ml/hr, temperature 4° C. and 10 ml fractions were collected.

The eluate was continuously monitored for 280 nm light absorption and the results are shown in FIG. 1. Peaks were observed at fraction numbers 12, 60, 100 and 120. PHILIP activity based on the bioassaytest described in example 3, was found in fraction nos. 75–100. Transferrin showed peak activity at fraction no 95. Haptoglobin showed peak activity at fraction 54. Standard immunological tests were used to measure activity of transferrin and haptoglobin.

Figure 2:
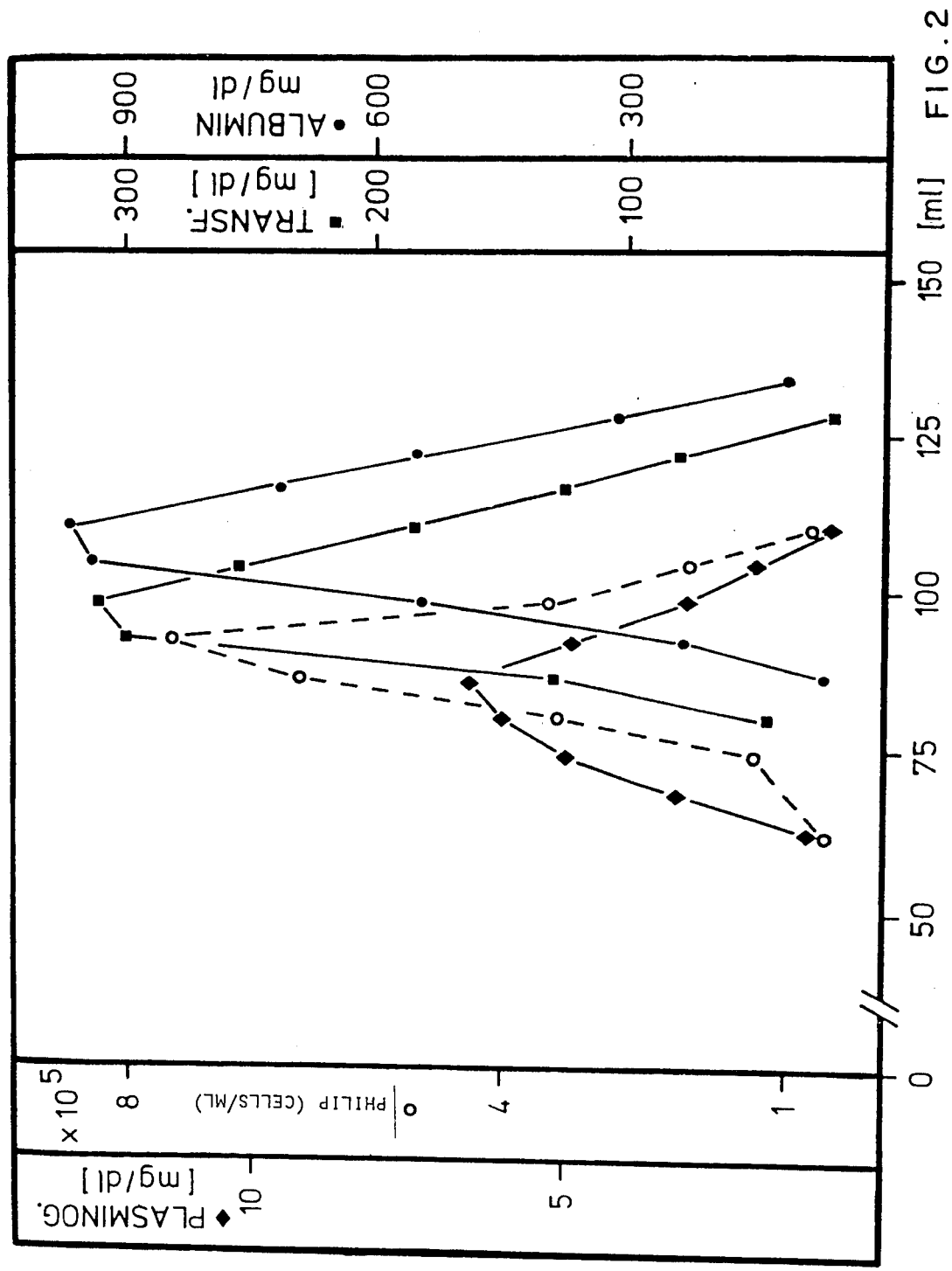
FIG. 2 is a plot of light transmission (%) versus elution volume for the separation of the biologically active fractions (Nos. 75-100) obtained in Example 1 after refractionation on a Sephadex G 150 chromatography column.

The results of refractionating pooled fractions 75–100 (concentrated to 25 ml against polyethyleneglycol) on a Sephadex G-150 column (20×900 mm); 4 ml/hr flow; 0,05 M phosphate buffer containing 0,1 M NaCl; is shown in FIG. 2. 3 ml fractions were collected. The different biological activities can be clearly distinguished by the separated peaks.

Figure 3:
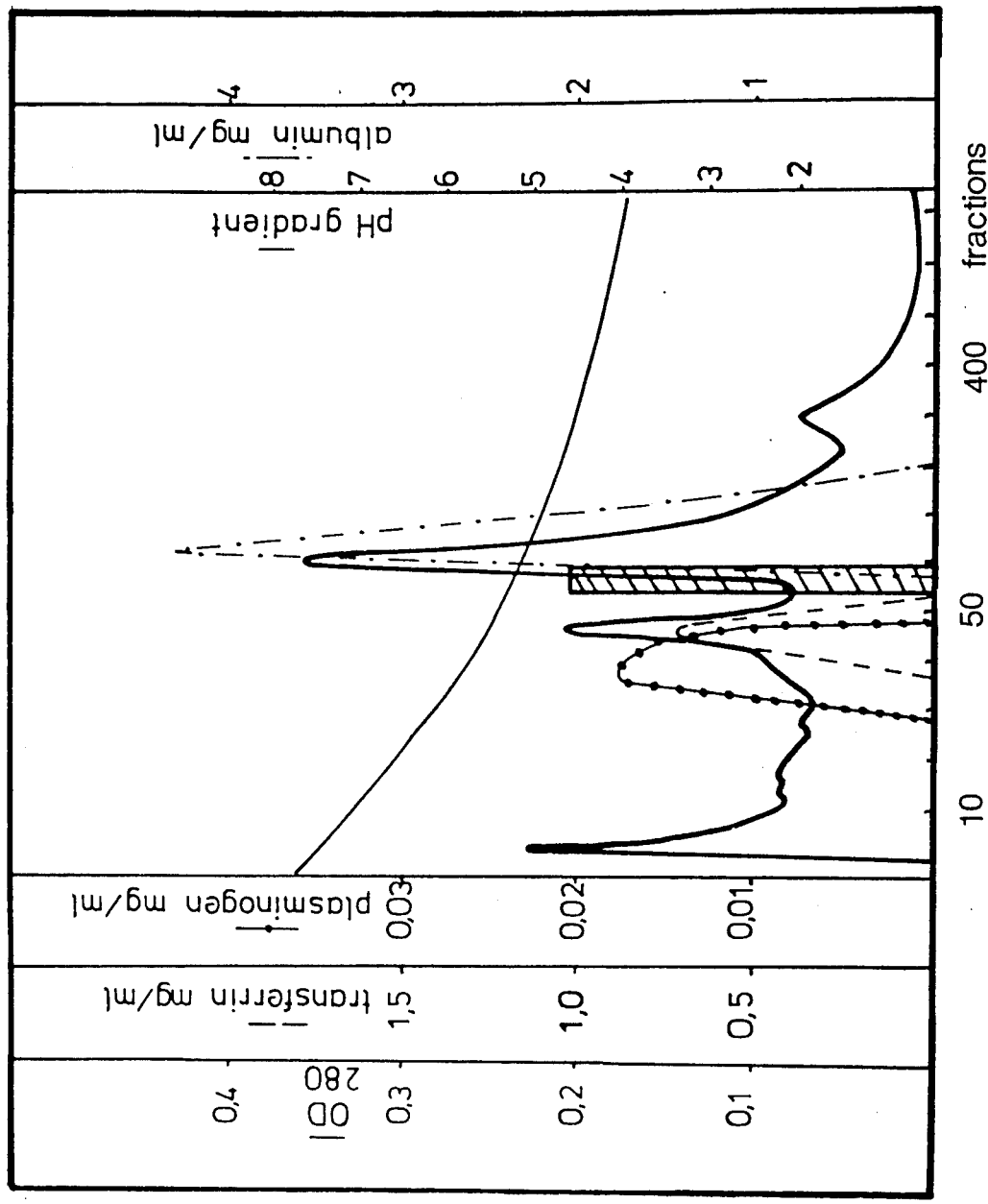
FIG. 3 is a plot showing the results of chromatofocussing the biologically active fractions (Nos. 75-100) obtained in Example 1 in terms of biological and immunological activity.
Figure 4:
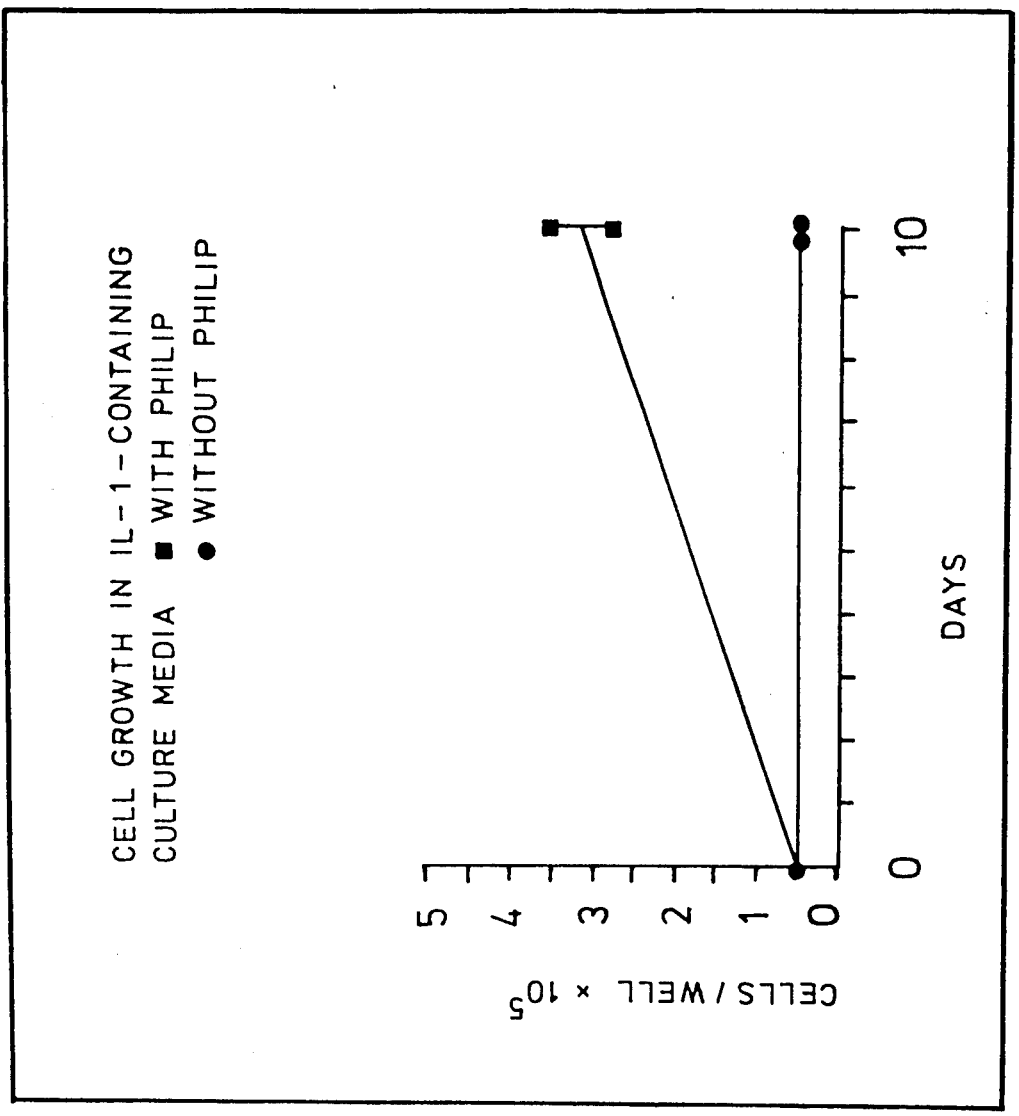
FIG. 4 is a graph showing the results obtained in Example 7 for the production of Interleukin 2 in the presence and in the absence of the novel blood serum glycoprotein of this invention.

Further differentiation of the biological activity of PHILIP and transferrin and plasminogen is clearly demonstrated by FIG. 3 showing chromatofocussing of the pooled fractions 75–100 from the G-200 column.

EXAMPLE 2

Affinity chromatography of PHILIP 10 ml of PHILIP isolated by column chromatography as described in example 1 is dialysed against 50 mMol/1 phosphate buffer, pH 7,0 before application to affinity columns. Columns containing WGA and Blue A and ConA are purchased from Pharmacia, Uppsala, Sweden. Covalent coupling of 1-lysine to sepharose 4B (purchased from Pharmacia, Sweden) is performed according to the method described by Deutsch and Merz. (Deutsch D. G., Mertz E. T.: (1970), Science vol. 170, pp. 1095–1096).

4 ml of PHILIP is layered into 2 ml of the affinity gels by slow addition, drop by drop. The column is incubated at room temperature for 60 minutes whereafter the non-adsorbed material is eluted by a 50 mMol/l phosphate buffer, pH 7,0. A buffer volume of 50 ml is used. Then the adsorbed material is eluted by use of a 50 mMol/l phosphate buffer, pH 7,0 containing N-acetyl D glucosamine in a concentration of 200 mMol/l in the case of WGA, alpha-D-mannopyranoside 200 mMol/l in the case of ConA, epsilon-amino capronic acid 200 mMol/l in the case of lysine and NADPH in the same concentration dissolved in the same buffer containing additionally 50% ethylene glycol and 20% NaCl in the case of Blue A. The eluted samples—for each column two 50 ml portions are eluted—are concentrated by polyethylene glycol to an end volume of 2 ml and dialysed against RPMI exhaustively. PHILIP is recovered from WGA-sepharose in the second specific eluate.

EXAMPLE 3

Biological test for PHILIP activity 10 ml of the collected fraction from the column chromatography in example 1 is dialyzed against 200 ml of RPMI 1640. The dialysis is performed at 4° C. Thereafter the preparation is sterilized by filtration through a 0,22 um sterile filter which is available from different commercial sources and pipetted into microtiter plates which have been prefilled with RPMI 1640 to a volume of 200 ul/ well, so that in the first well of a row 200 $\mu$l PHILIP is mixed to the preexisting RPMI. After mixing the volume of 200 $\mu$l is transferred to the second well of the row and so on, until a dilution of 1:32 has been achieved. 50000 cells which have been incubated at 37° C., 98% humidity and 10% $CO_2$ in the serum-free RPMI for 24 hours are added in a volume of 20–50 $\mu$l to each well in the microtiter plate. PHA is added to a final concentration of 4 ug/ml to each well. The microtiter plate is incubated for 7 days under the conditions described above. On day 7 the plate is assayed for cell growth by counting the cells in an electronic cell counter. The dilution of th PHILIP preparation in which the cell number has doubled (i.e. reached 100,000) is considered as the inverse of the titer. If for example the cell number has increased to more than 100,000 in the dilution of 1:8, the titer in the preparation in considered to be 8.

EXAMPLE 4

Inactivation of PHILIP by trypsin and by neuraminidase enzymes.

(a) Inactivation by trypsin 10 ml samples of PHILIP obtained by column chromatography as described in example 1 are incubated at 37° C. in presence of trypsin (4x crystallized, obtained e.g. from SERVA Chemical Corp., Heidelberg, FRG) concentration 0,1% w/v in phosphate buffer, pH 7,0 in the presence of 50 mMol/l CaCl2. After 120 min. incubation, EDTA is added in a concentration of 0,01 mMol/l whereafter the samples are incubated again at 37° C. for 120 min. After this second incubation 10 mMol/l DFP is added to the sample in order to inhibit the trypsin which is a serine protease.

The sample is dialysed against 200 ml RPMI with a dialyzing membrane pemeable to substances having molecular weight below about 15,000 and tested for biologic activity according to the test method described in example 3. No biological activity was observed.

(b) Inactivation by neuraminidase

Neuraminidase isolated from *Clostridium botulinus* which is readily commercially available is covalently coupled to BrCN-activated Sepharose 4B manufactured by Pharmacia, Uppsala, Sweden, whereafter the gel is thoroughly rinsed in Phosphate buffer. PHILIP samples as described in part (a) of this example, are layered onto the top of columns with a gel content of 2 ml and incubated at 37° C. for 6 hours under sterile conditions. Thereafter the sample is eluted by phosphate buffer, pH 7,0 and dialysed against RPMI 1640 as described above. The biologic activity of PHILIP is determined according to the microtiter bioassay technique described above in example 3. No biological activity was observed.

EXAMPLE 5

Production of an Interleukin-1 preparation free of mitogen and serum proteins (a) Preparation by use of adherent pro-macrophages Blood lymphocytes are isolated as described in example 1 of the above mentioned U.S. Pat. No. 4,390,623. After washing with sterile culture medium, the cells, usually 400 to 800 millions isolated per 400 ml whole blood, are incubated 60 minutes at 37° C. in RPMI 1640 under standard cell culture conditions. The incubation is performed on a plastic petri dish with a diameter of 15 cm. Such dishes are commercially readily available. After incubation, the cell containing medium is poured off the dish, and the dish with the adhering cells, usually 10% of the total cell number is rinsed several times, usually 6, with RPMI 1640 to remove all non-adherent cells. Thereafter the adherent cells are removed from the dish by use of a rubber policeman, counted and suspended in a concentration of 3 millions/ml in RPMI 1640 and incubated 24 hours at 37° C. under standard cell culture conditions before further processing. After incubation the cells are stimulated with PHA for 4 to 12 hours preferably 4 to 8 hours, most preferably 4 hours at a concentration of 4 μg PHA/ml of culture medium. The PHA is then discarded, the cells washed 3 times as described above, whereafter the cells are incubated in RPMI 1640 without supplements for 18–24 hours, preferably 20 hours. The culture supernatants are collected whereafter the cells can be stimulated again with PHA if so desired. The stimulation may be repeated up to 3 times if so desired. The serum free culture supernatants can be concentrated on a YM 10 membrane as described in example 1 of U.S. Pat. No. 4,390,623, if desired. The IL-1 containing supernatants can be stored at −20° until they are used.

(b) Preparation by use of isolated blood lymphocytes without separation of adherent macrophages Blood lymphocytes are isolated as described above in this example. The cells after washing with RPMI 1640 are incubated at 37° C. under standard cell culture conditions for 24 hours. Thereafter the cells are counted and stimulated with PHA at a concentration of 4 μg/ml culture medium and a cell density of 3 millions/ml as described above in this example. All remaining steps of the preparation of IL-1 are the same as those mentioned above in this example.

EXAMPLE 6

Biological test for Interleukin-1 activity

Interleukin-1, free of lectin and sera, prepared as described in example 5 is filtered sterile and tested for its biological activity as follows:

RPMI 1640 is mixed with either 15% inactivated human AB serum or with PHILIP to a titer of 8 in the end volume. 200 μl thereof is introduced into the top row of wells in a microtiter plate. In the 4 following rows 100 ml of the mixture is applicated to each well. 200 μl of the Il-1 is added to the wells of the top row and mixed with the RPMI 1640 suplemented by serum PHILIP. 100 μl is transferred to the next row, mixed and so on. Thus a serial dilution of Il-1 in dilution steps of 1:2 is achieved. 20 to 50 μl of isolated blood lymphocytes as described in example 1 of U.S. Pat. No. 4,390,623 are added. As a consequence of the interaction of Il-1 and PHILIP, the cells start synthesizing Il-2. The effectiveness of the synthesis is dependent on the concentration of Il-1. Il-1 activity is quantificated by the titer it exhibits in the culture (i.e. by the inverse of the dilution in which the cell number has doubled within seven days in culture). (See FIG. 4)

EXAMPLE 7

Production of Interleukin-2 by use of PHILIP (a) Production of Interleukin-2 by use of PHILIP and PHA Peripheral blood lymphocytes isolated as described above, after washing 3× with RPMI 1640, are suspended in a mixture of RPMI 1640 and PHILIP isolated as described above in example 1. PHILIP is present at a concentration of 1:1 to 1:32, usually 1:16. The concentration of PHILIP is determined by its biological activity, which is assayed according to example 3. A titer of 8 in the end volume is desired. The cells are suspended at a concentration of 3 millions/ml and stimulated 4 to 24 hours with PHA in a concentration of 4 μg/ml. The stimulation time is preferably 8–20 hours, most preferably 8–12 hours. After stimulation, the cells are washed 3 times as described above, and used to condition the culture medium at a concentration of 3 millions/ml in absence of other supplements than those contained in RPMI 1640. The conditioning time should be 18–24 hours, most preferably 20 hours. Thereafter the cells are spun down and the culture medium collected. The stimulation step might be repeated up to 3 times, if so desired. The conditioned medium can, if desired, be concentrated on a YM 10 membrane as described above. Interleukin-2 activity can be assayed by either one of the two biological tests described above in this application. The activity of IL-2 will rise as a direct function of the degree of concentration. The medium containing PHA and PHILIP can be re-used up to 3 times for generation of IL-2.

(b) Production of Interleukin-2 by use of PHILIP and Interleukin-1

Mitogen- and serum-free IL-1 preparations as described above in this application are mixed with PHILIP isolated according to the method described above in this application in such a proportion that PHILIP will be present in a final titer of 8. The so prepared culture medium is used under the same conditions as is PHA and PHILIP containing culture medium used in this example. The processing of the IL-2 preparation is the same as described above in this example.

EXAMPLE 8

Inhibition of blast transformation and of continuous Il-2 dependent T-cell growth by serine esterase inhibitors Cells used for blast formation assay are cells which according to the method described above have been incubated 24 hours in serum free RPMI for 24 hours. Cells used for testing the Il-2 dependent T-cell growth are derived from a continuously growing T-cell line kept in culture in our laboratory. The preparations to be inactivated by serine esterase inhibitors are incubated either with DFP (diisopropylfluorophosphate) in a concentration of 0,0024 ml per ml preparation (usually 5 ml preparation to be tested is mixed with 60 ul of DFP), or with PMSF (phenylmethylsulfonylfluoride) in a concentration of 50 mMol/l of preparation to be tested. The inactivation is performed at 0° C. After 60 minutes, the preparation is transferred into dialysis bags and dialysed against 1000 ml of RPMI for 6 hours. Then the RPMI is changed against the same volume of fresh RPMI and dialysis is continued for 24 hours at 4° C. The biological test is performed in the following way:

The inactivated preparations are transferred to microtiter plates after they have been sterilized by filtration as described in example 4. Cells are added to the wells at a concentration of 50000/well, and the cell number is counted on day 7 as described in example 4. Cell counts less than 100,000 are considered indicative of loss of Il-2 activity. In our experiments we have always either yielded cell counts either of more than 100,000 or less than 50,000 which was the cell number introduced to the well. Usually a positive test yields cell counts of 400,000 to 600,000.

What is claimed is:

1. A method for preventing T-cell blast formation comprising adding a serine esterase enzyme inhibiting alkylating agent to a system containing Interleukin-1, T-cell growth factor, and peripheral blood T-cell lymphocytes, thereby preventing T-cell blastogenesis.

2. The method of claim 1 wherein said alkylating agent is selected from the group consisting of diisopropylfluorophosphate and phenylmethyl sulfonic fluoride.

* * * * *